United States Patent [19]

Schubart et al.

[11] Patent Number: 5,028,729

[45] Date of Patent: Jul. 2, 1991

[54] PROCESS FOR THE PRODUCTION OF BIS-(DIALKOXYTHIO-PHOSPHORYL)-TRI-SULFIDES

[75] Inventors: Rüdiger Schubart, Bergisch Gladbach; Hans-Wilhelm Engels, Kerpen, both of Fed. Rep. of Germany

[73] Assignee: Bayer Aktiengesellschaft, Leverkusen, Fed. Rep. of Germany

[21] Appl. No.: 474,323

[22] Filed: Feb. 2, 1990

[30] Foreign Application Priority Data

Feb. 14, 1989 [DE] Fed. Rep. of Germany ....... 3904290
Dec. 22, 1989 [DE] Fed. Rep. of Germany ....... 3942464

[51] Int. Cl.$^5$ .............................................. C07B 9/17
[52] U.S. Cl. ..................................... 558/129; 558/151
[58] Field of Search ................................ 558/129, 151

[56] References Cited

FOREIGN PATENT DOCUMENTS 2249090 4/1973 Fed. Rep. of Germany .
1401435 7/1975 United Kingdom .

OTHER PUBLICATIONS

Soviet Inventions Illustrated, Section Ch: Chemical, Week C48, SU-644-306, "Prepn. of di:alkoxy-thiophosphoryl-di:alkyl-amino . . .", Jan. 14, 1981.

Primary Examiner—Mukund J. Shah
Assistant Examiner—Jyothsna Venkat
Attorney, Agent, or Firm—Connolly and Hutz

[57] ABSTRACT

The elminination of sulfur from bis-(dialkoxythiophosphoryl)-tetrasulfides to bis-(dialkoxythiophosphoryl)-trisulfides on certain silicate fillers, carbon black and aluminium oxide is quantitative.

9 Claims, No Drawings

PROCESS FOR THE PRODUCTION OF BIS-(DIALKOXYTHIO-PHOSPHORYL)-TRISULFIDES

This invention relates to a process for the production of bis-(dialkoxythiophosphoryl)-trisulfides (hereinafter referred to as "P-$S_3$") by elimination of sulfur from bis-(dialkoxythiophosphoryl)-tetrasulfides (hereinafter referred to as "P-$S_4$") on sodium aluminium silicate respectively on fillers selected from the group consisting of silicates, carbon black and aluminium oxide which fillers have been treated with alkali or alkali earth hydroxide.

The use of P-$S_4$ and—preferably—P-$S_3$ as a sulfur donor or ultra-accelerator in the vulcanization of rubber is known (DE-OS 19 36 694 and 22 49 090). According to this literature, these compounds may be prepared by reaction of dialkyl dithiophosphoric acid with sulfur dichloride ($SCl_2$, dichlorosulfane) to P-$S_3$ or with sulfur monochloride ($S_2Cl_2$, dichlorodisulfane) to P-$S_4$, optionally in the presence of a base, such as sodium hydroxide, and optionally in an organic solvent.

Sulfur dichloride disproportionates readily to sulfur monochloride and chlorine, so that on the one hand the presence of the aggressive chlorine has to be taken into account and, on the other hand, the sulfur dichloride always undergoes partial disproportionation under reaction conditions, with the result that, in addition to the desired P-$S_3$, the less active and therefore less desirable P-$S_4$ is also formed.

It has now surprisingly been found that P-$S_4$ expels sulfur in the presence of certain fillers and changes into P-$S_3$. This discovery can be used in two ways. Firstly, it enables the P-$S_3$ permeated by P-$S_4$ to be processed to pure P-$S_3$, providing the synthesis has been carried out with sulfur dichloride. Secondly, it affords the possibility of synthesizing P-$S_4$ as an intermediate using the more pleasant sulfur monochloride and subsequently quantitatively converting the P-$S_4$ thus formed into the desired P-$S_3$ by elimination of sulfur.

Accordingly, the present invention relates to a process for the production of bis-(di-$C_{1-6}$-alkoxythiophosphoryl)-trisulfides from bis-(di-$C_{1-6}$-alkoxythphosphoryl)-tetrasulfides by elimination of sulfur on sodium aluminium silicate and/or on fillers selected from the group consisting of silicates, carbon black and aluminium oxide which fillers have been treated with alkali or alkali earth hydroxide.

Preferred starting and end products are those in which "alkoxy" stands for methoxy, ethoxy, n- and isopropoxy, n-, sec.- and isobutoxy, n-hexoxy, cyclohexoxy; the most important meaning is ethoxy.

Based on the product dried at 105° C., preferred sodium aluminium silicates contain at least 3% by weight $Na_2O$, at least 3% by weight $Al_2O_3$ and at least 60% by weight $SiO_2$ according to DIN 55 921/2 and preferably 6 to 8% by weight $Na_2O$, 6 to 8% by weight $Al_2O_3$ and at least 75% by weight $SiO_2$. They have a BET surface of 60 to 70 $m^2/g$ and a pH value (according to DIN 53 200) in the range from 10 to 12. A preferred sodium aluminium silicate of this type is commercially obtainable, for example, as ®Vulkasil Al (a product of Bayer AG, Leverkusen).

Fillers suitable for the process according to the invention include the silicates such as, for example, calcium silicate, aluminium silicate, magnesium silicate, silicon dioxide, carbon black and aluminium oxide provided that they have been treated with alkali and/or alkali earth hydroxide.

The specific surfaces of particularly preferred silicate fillers range from 300 to 650 $m^2/g$, of particularly preferred carbon black from 5 to 250 $m^2/g$ and of particularly preferred aluminium oxide from 100 to 250 $m^2/g$.

A recommended method for the production of P-$S_4$ starts out from phosphorus pentasulfide and a monohydric alcohol. This process is described in the following with reference, by way of example, to the diethoxy compound:

Phosphorus pentasulfide is reacted at 20° to 80° C. with an equivalent quantity or an excess of up to 0.1 equivalent ethanol in an inert water-immiscible organic solvent, for example toluene, to form the crude diethyl dithiophosphoric acid which is then converted into the corresponding sodium salt by neutralization with aqueous sodium hydroxide in the presence of 1 to 5% by weight sulfur, based on phosphorus pentasulfide (the sulfur is used for sulfurization of any secondary products formed). The organic phase is separated off and sulfur monochloride is added to the aqueous phase, preferably in the absence of organic solvent, at a temperature below 40° C. and preferably at a temperature in the range from about 10° to 20° C. and the P-$S_4$ accumulates in a high yield. For separation from the aqueous phase, the P-$S_4$, which is insoluble in water, is best heated to a temperature above its melting point (44° to 45° C.), for example to 45° to 50° C., and is separated in molten form from the aqueous phase containing the sodium chloride formed, by removal of that phase. The liquid P-$S_4$ may be dried in vacuo, preferably at 50° to 55° C.

The P-$S_4$ may be mixed with the filler in any suitable mixer, for example in a powder mixer, in a mixing screw or in a fluidized-bed mixer. The mixing ratio may vary within wide limits and generally amounts to between 3 and 100% by weight and preferably to between 34 and 60% by weight of filler, based on the P-$S_4$ used.

For manufacturing the hydroxide-treated filler, the filler is suspended in an aqueous solution of alkali hydroxide respectively earth alkali hydroxide. This suspension is evaporated in vacuo and dried at elevated temperature as, for example, at 100° C. After pulverization in a suitable equipment, the hydroxide-treated filler is ready for use.

In general, the hydroxide will be used in a quantity of from 0.1 to 20 g, preferably from 0.1 to 10 g, in particular from 0.5 to 5 g (dissolved in a sufficient amount of water) per 100 g of filler.

Sodium hydroxide, potassium hydroxide and calcium hydroxide are preferred.

The P-$S_4$ is optionally present in liquid-form before mixing because it tends to form supercooled melts through a delay in crystallization.

For the process according to the invention, the mixture of P-$S_4$ and filler is left standing at 10° to 80° C., preferably at 10° to 45° and more preferably at 10° to 30° C. until the conversion of the P-$S_4$, as measured from the ratio of residual to original P-$S_4$, comprises at least 95%, preferably at least 98% and more preferably at least 99%. In the case of the diethoxy compound, this target is generally achieved after 6 days (at room temperature) where 30 parts by weight filler have been used to 70 parts by weight P-$S_4$. Where the ratio is 90:10, the reaction time (at room temperature) increases to ~20 days.

For practical application, it is often desirable to use the P-S$_3$ in the form of pellets or cyclindrical pellets. The pelletizing step may be carried out both after the mixing step and before storage for the elimination of sulfur and also after the reaction to P-S$_3$.

The mixture of (i) P-S$_3$, (ii) filler and (iii) sulfur obtained by the process according to the invention, may be used for the vulcanization of rubber with no need for the products (ii) and (iii) to be separated. The P-S$_3$ may of course also be dissolved out from this mixture with a suitable organic solvent, for example with toluene or dichloromethane.

EXAMPLE

Production of P-S$_4$ 400 g ethanol were added dropwise, with stirring and cooling to 444 g phosphorus pentasulfide in 300 ml toluene. After the dropwise addition, the temperature is increased to 80° C. in steps of 10° C. After the elimination of hydrogen sulfide, the reaction mixture was cooled to 10° to 20° C. 20 g sulfur were added and a mixture of 160 g sodium hydroxide and 320 ml water was added dropwise with cooling. After stirring for 1 hour, the toluene phase was separated off and the aqueous phase was extracted once more with 300 ml toluene. The toluene phases were discarded.

257 g sulfur monochloride were added dropwise to the aqueous phase with rapid stirring at 10° to 20° C. After stirring for 15 minutes, 10 g potassium carbonate were added. After stirring for another 2 hours at 10° to 20° C., the reaction mixture was heated to 45° to 50° C. and the melt formed was separated from the aqueous phase, washed once more with warm water and dried in vacuo. 806 g of a yellow oil (=bis-(diethoxythiophosphoryl)-tetrasulfide) were obtained.

Production of P-S$_3$ 1. 780 g of liquid P-S$_4$ were added with stirring (powder mixer) and cooling (ice bath) to 335 g sodium aluminium silicate (®Vulkasil Al, Product of Bayer AG) so rapidly that the temperature did not exceed 30° C. The powder obtained was stored at room temperature. After 6 days, the conversion of P-S$_4$ to P-S$_3$ was quantitative.

2. 70 g of liquid P-S$_4$ were admixed with 30 g of a powder (obtained by mixing 100 g of silicic acid (®Sipernat 50, P$_H$ 6, specific surface 170 m$^2$/g, product of Degussa AG) and 1 g of calciumhydroxide in water, then drying in vacuo (finally at 100° C.) and subsequently pulverizing). After 10 days storage at room temperature the conversion of P-S$_4$ to P-S$_3$ was nearly quantitative.

3. 70 g of liquid P-S$_4$ were admixed with 30 g of a powder (obtained by mixing 100 g of active precipitated silic acid (®Vulkasil S, product of Bayer AG) and 5 g of potassium hydroxide in water, then drying in vacuo (finally at 100° C.) and subsequently pulverizing) under temperature control so that the temperature did not exceed 30° C. After storage at room temperature for 10 days, the conversion from P-S$_4$ to P-S$_3$ was complete.

4. The process 3, described above, was repeated with the difference, that 3 g of sodium hydroxide were used instead of 5 g of potassium hydroxide. After storage at room temperature for 12 days, the conversion from P-S$_4$ to P-S$_3$ was complete.

We claim:

1. A process for the production of bis-(di-C$_{1-6}$-alkoxythiophosphoryl)-trisulfides from bis-(di-C$_{1-6}$-alkoxythiophosphoryl)-tetrasulfides by elimination of sulfur on sodium aluminium silicate or on a filler selected from the group consisting of silicates, carbon black and aluminium oxide which fillers have been treated with alkali or on a earth alkali hydroxide.

2. A process as claimed in claim 1 for the production of bis-(diethoxythiophosphoryl)-trisulfide from bis-(diethoxythiophosphoryl)-tetrasulfide.

3. A process as claimed in claims 1, in which the sodium aluminium silicate used contains at least 3% by weight Na$_2$O, at least 3% by weight Al$_2$O$_3$ and at least 60% by weight SiO$_2$.

4. A process as claimed in claims 1, in which the sodium aluminium silicate used contains 6 to 8% by weight Na$_2$O, 6 to 8% by weight Al$_2$O$_3$ and at least 75% by weight SiO$_2$.

5. A process as claimed in claim 1 in which the filler used has been treated with 0.1 to 20 g of alkali or alkali earth hydroxide per 100 g of filler.

6. A process as claimed in claim 1 in which the filler used has been treated with 0.2 to 10 g of alkali or alkali earth hydroxide per 100 g of filler.

7. A process as claimed in claim 1, in which the filler used has been treated with 0.5 to 5 g of alkali or alkali earth hydroxide per 100 g of filler.

8. A process as claimed in claim 1, in which the hydroxide used is selected from the group consisting of sodium hydroxide, potassium hydroxide and calcium hydroxide.

9. A process as claimed in claim 1, in which the silicate filler is selected from the group consisting of calcium silicate, magnesium silicate, aluminium silicate and SiO$_2$.

* * * * *